US00PP30738P2

(12) United States Plant Patent
Hansen

(10) Patent No.: US PP30,738 P2
(45) Date of Patent: Jul. 23, 2019

(54) ***HIBISCUS* PLANT NAMED 'CHERRY CHOCO LATTE'**

(50) Latin Name: ***Hibiscus* hybrid (L.)**
Varietal Denomination: Cherry Choco Latte

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 15/731,016

(22) Filed: Apr. 7, 2017

(51) Int. Cl.
*A01H 5/02* (2018.01)

(52) U.S. Cl.
USPC ..... Plt./257

(58) Field of Classification Search
USPC ..... Plt./257
See application file for complete search history.

*Primary Examiner* — Annette H Para

(57) ABSTRACT

A new and distinct cultivar of winter-hardy, herbaceous, perennial, hybrid *Hibiscus* plant named Cherry Choco Latte' comprising a compact slightly spreading habit of multiple, well-branched, basal stems having flowers over a long season with near white petals having sharply contrasting magenta veins and large deep red eye. The heavy substance petals have a fold on the leading edge and are slightly ruffled at the apex giving the flower the ability to withstand harsh winds and rains. The three to five-lobed, deeply-dissected foliage is mahogany colored when young or when exposed to high light intensity and becomes dark green with purple mahogany blushing when mature.

1 Drawing Sheet

Botanical classification: *Hibiscus* hybrid (L.).
Variety denomination: 'Cherry Choco Latte'.

BACKGROUND AND ORIGIN OF THE PLANT

The present invention relates to the new and distinct winter-hardy, herbaceous, *hibiscus* plant, *Hibiscus* 'Cherry Choco Latte' hybridized under direction of the inventor on Aug. 30, 2012 at a wholesale perennial nursery in Zeeland, Mich. The new plant is a single seedling selection from among the cross between *Hibiscus* 'Cherry Cheesecake' U.S. Plant Pat. No. 26,089 times an unnamed hybrid named 11-117 (not patented). The seeds were harvested in the fall of 2012 and the single unique plant among the resultant seedlings which passed the initial trial in the summer of 2014 was assigned the breeder code # 12-151-4. Both parents have a complex mixture of species in them, most likely comprising the species: *moscheutos, grandiflorus* and *coccineus*. *Hibiscus* 'Cherry Choco Latte' was first asexually propagated in 2014 by sterile shoot-tip tissue culture at the same nursery in Zeeland, Mich. The resultant asexually propagated plants have been found to be stable and true to type in successive generations of asexual reproduction.

No plants of *Hibiscus* 'Cherry Choco Latte' have been sold by any name, either in this country or anywhere in the world, prior to the filing of this application, nor has any disclosure been made prior to the filing of this application with the exception of that which was sold or disclosed within one year of the filing of this application and was derived directly or indirectly from the inventor.

BRIEF SUMMARY OF THE PLANT

*Hibiscus* 'Cherry Choco Latte' differs from its parents as well as all other hardy herbaceous *hibiscus* known to the applicant in many traits. The most similar *hibiscus* in flower color known to the applicant are 'Starry Starry Night' U.S. Plant Pat. No. 27,901, 'Summer Storm' U.S. Plant Pat. No. 20,443, 'Perfect Storm' U.S. Plant Pat. No. 27,880 and the female parent. Compared with 'Starry Starry Night' the new plant has a broader and shorter habit, the foliage of the comparison plant are darker mahogany tinted and the flowers of the new plant are have a thicker substance, tend to have a fold on the leading edge of the petal and the contrast in the magenta veining and white between the veins is greater. Compared with 'Summer Storm' the new plant has a broader, shorter and more compact habit, the foliage is darker green rather than mahogany, the flower has greater contrast in the vein color and surrounding white petal area and the petal apex tends to have deeper magenta concentration rather than the veins and center of 'Summer Storm' becoming increasingly lighter pigmented as they reach the apex. 'Perfect Storm' differs in having mahogany-colored foliage and less contrasting petal veins and color between the veins. The female parent, 'Cherry Cheesecake', has similar flower form but less intense magenta pigmenting in the veins and the habit of the new plant is shorter and more compact. The male parent has a taller habit, and the flowers of the male parent are entirely deep magenta with a darker red eye.

*Hibiscus* 'Cherry Choco Latte' is a unique hardy herbaceous *hibiscus* with the following combined traits:

1. Winter-hardy, perennial with short, compact, slightly spreading habit of multiple, well-branched, basal stems.
2. Many rotate flowers over a prolonged season.
3. Flower petals having near white background with strongly contrasting deep magenta veining, a slight tint of magenta toward the petal apex and notably large, deep-red eye zone from which the veins radiate.
4. Flower shape is round with a flattened face except for the folding in the leading or inside petal edge and ruffling toward the apex which produces a more three-dimensional flower better able to withstand harsh winds and rains.

5. Dark green, deeply-dissected, primarily tri-lobed foliage, with a blush of purple mahogany.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
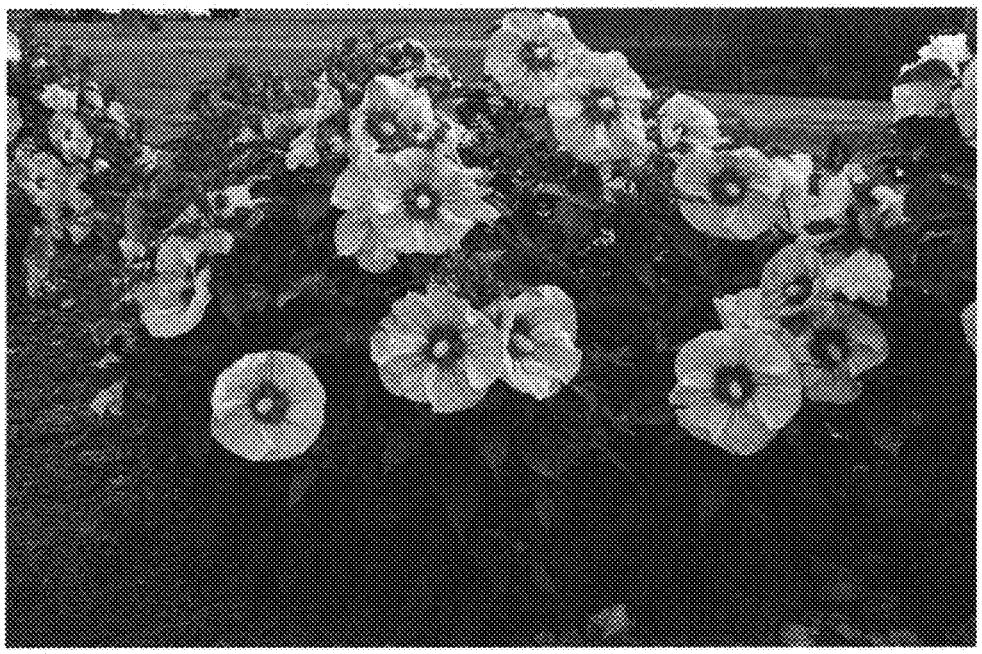
FIG. 1 shows a three-year-old plant in the landscape in mid-season.
Figure 2:
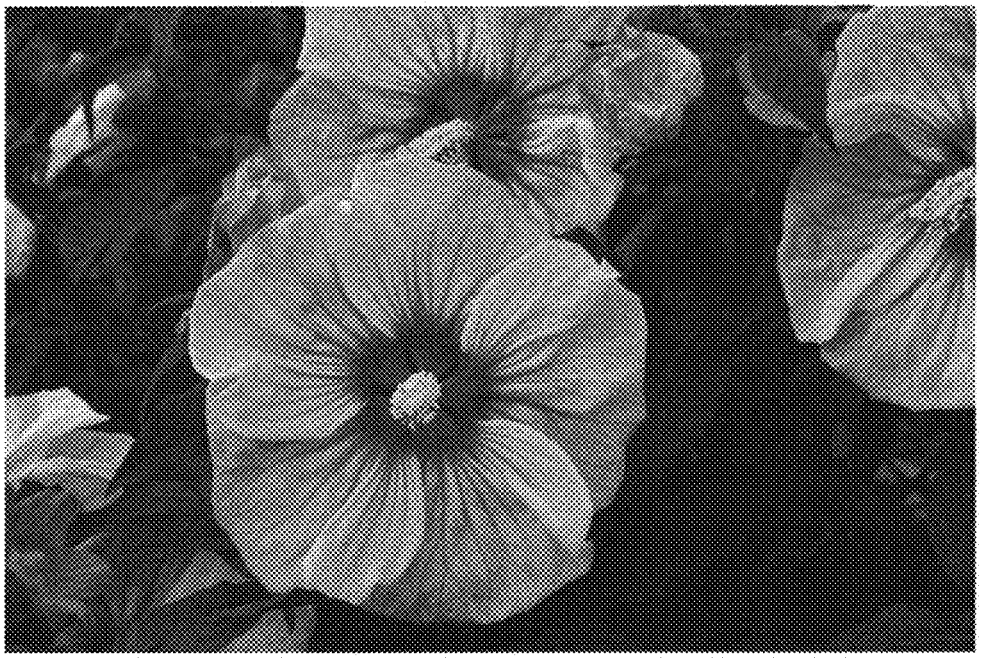
FIG. 2 shows a close-up of the flower.

The following descriptions and color references are based on the 2001 edition of The Royal Horticultural Society Colour Chart except where common dictionary terms are used. The new plant, *Hibiscus* 'Cherry Choco Latte', has not been observed under all possible environments. The phenotype may vary slightly with different environmental conditions, such as temperature, light, fertility, moisture and maturity levels, but without any change in the genotype. The following observations and size descriptions are of a three-year-old plant in the loamy-sand, open-field full-sun trials of a nursery in Zeeland, Mich. with supplemental fertilizer and water as needed. The plants are of natural habit without treatment of plant growth regulators, nor pinching at any time in the growth year.

Parentage: Female (seed parent) *Hibiscus* 'Cherry Cheesecake'; male (pollen parent) 11-117 which is a hybrid between 'Crown Jewels' U.S. Plant Pat. No. 11,857 and 'Midnight Marvel' U.S. Plant Pat. No. 24,079;

Propagation:

*Method*.—Stem cuttings and sterile shoot-tip plant tissue culture division.

*Time to initiate roots from tissue culture*.—About two weeks.

*Rooting habit*.—Normal, branching, developing thick to about 2.8 cm diameter, fleshy; root color creamy yellow between RHS 161D and lighter than RHS 159D depending on soil type.

*Crop time*.—Under normal summer growing conditions 12 to 16 weeks to flower in a four-liter container from cutting. Plant vigor is very good.

Plant description:

*Plant habit*.—Hardy herbaceous perermial with about twenty-seven thick upright and heavily branched main stems producing a upright spreading mound to about 127.0 cm tall and about 165.0 cm wide; about seven primary branches per main stem protruding at about 55° above horizontal; flowering from base to top of plant with up to about fifty-five flowers per main stem.

*Stem*.—Terete, glabrous, glaucous; average about 118.0 cm tall and average about 2.0 cm diameter at base.

*Stem color*.—Nearest RHS 146D.

*Lateral branches*.—Average about seven per stem; terete, glabrous, glaucous; to about 60.0 cm long and 15.0 mm diameter, average about 35.0 cm long and about 11.0 mm diameter at base.

*Lateral branch color*.—Nearest RHS 146D.

*Internode*.—About 18 nodes per stem below flowers, average internode length about 4.7 cm of unpinched plant below flowers.

*Internode color*.—Same as surrounding stem.

Foliage description: Alternate; coarsely and irregularly dentate; apical and lateral lobes acute; base broadly rounded to hastate; glabrous; deeply cleft nearly to petiole, typically three to five-lobed; adaxial and abaxial surface matte, slightly pulverulent; leaf blades to about 21.0 cm long and about 17.0 cm across, average leaf blade size 16.0 cm long and 14.0 cm wide; no fragrance detected;

*Foliage color*.—Mature upper leaves adaxial surface nearest RHS N187C with intense light exposure, lower leaves with less light nearest RHS 139A with blush of nearest RHS N187C; mature abaxial nearest RHS 147B with blush of nearest RHS N187C; young adaxial nearest RHS N187C; young abaxial nearest RHS 147B with blush of nearest RHS N187C.

*Veins*.—Palmate; lustrous; costate on abaxial.

*Vein color*.—Adaxial upper leaves nearest RHS 187C, nearest RHS 185B on lower leaves and nearest RHS 187B on young leaves; abaxial nearest RHS 183C.

*Petioles*.—Mostly terete, slightly flattened on adaxial side; glaucous; glabrous; size to about 8.0 cm long and 5.5 mm wide at base.

*Petiole color*.—Upper leaves adaxial nearest RHS 183C, lower leaves nearest RHS 146C tinted with RHS 183C and young adaxial nearest RHS 183A; abaxial lower leaves nearest RHS 146D, upper leaves nearest RHS 183D and young leaves nearest RHS 183C.

Flower description: Complete; actinomophic; upward to outward facing; rotate; lasting up to two days on plant; effective for about 8 weeks from late July until late September; no fragrance detected;

*Buds two days prior to opening*.—Globoid with rounded apex and bluntly rounded base; carinate at sepal fusions; about 6.5 cm long and about 4.0 cm diameter in middle; sepals remaining adpressed to petals or with apices reflexed in terminal 5.0 mm.

*Buds one day prior to opening*.—Oblong with petals about 3.0 cm apart at apices and parallel to column; about 7.0 cm long and 6.5 cm diameter in center.

*Bud color*.—Petal color between veins nearest RHS 62D; veins in middle of petal lighter than RHS 62D with distal veins blushed between RHS 64A and RHS 64B.

*Epicalyx*.—Typically 12, rarely 13 per flower; entire, micro-puberulent; dull glabrous surface abaxial and adaxial; linear with sharply acute apex and truncate base, arcuate upwards near apex; about 2.4 cm long and base of about 2.5 mm wide.

*Epicalyx color*.—Adaxial nearest RHS 146C, abaxial nearest RHS 137B.

*Sepals*.—Five; glabrous; acute apex; fused base; margin entire, edentate; abaxial and adaxial surfaces matte; about 3.6 cm long, fused in about the basal 1.5 cm, about 2.5 cm wide at fusion, connate forming campanulate star-shaped calyx about 7.5 cm across and 3.0 cm deep.

*Sepal color*.—Adaxial nearest RHS 146D; abaxial nearest RHS 146C slightly maculate with RHS 184B; veins same as surrounding tissue.

*Flowers*.—Solitary, about 52 per main stem without pinching; flat-faced except for leading petal edge slightly folded and apex sinuate or ruffled; slightly upward to outwardly facing; average about 23.0 cm across and 8.0 cm deep from center to edge of petals; smaller in later part of flowering season; with lustrous deep red eye about 6.0 cm across.

*Petals*.—Five; glabrous toward center, microscopically and sparsely puberulent abaxial and adaxial distally; adnate to the androecium to form a column, imbricate to about 40% overlapping at widest part (petals overlapping about 40% of the petal portions on either side), palmately veined, primary and secondary veins slightly impressed on adaxial and costate abaxial; shape: rounded with distinct claw and limb; margins: entire, edentate; apex: rounded; base: short claw-like; size: average about 16.5 cm across, about 11.0 cm long and claw about 10.0 mm across at base (smaller in latter part of flowering season).

*Petal color*.—Adaxial eye between RHS 53A and RHS 53B, with veins radiating about the first 18.0 mm from eye nearest RHS 187C then central veins nearest RHS 53A and distal veins lightening to nearest RHS 64C, region between veins nearest RHS N155B; abaxial basal 1.5 cm near white nearest RHS 155D with about 4.0 mm wide stripe nearest RHS 60C, mid-petal nearest RHS 62D or lighter with distal perimeter blushing nearest RHS 60C, veins between RHS 62C and RHS 62D with some blushing near perimeter nearest RHS 60C.

*Gynoecium*.—Single; partially enclosed in column; Column: glabrous except base micro-puberulent, lustrous; about 5.0 cm long and about 9.0 mm wide at base; Column color: nearest RHS 53B in basal 5.0 mm and distally nearest RHS 155D; Style: micro-puberulent in region above column; protruding from column about 13.0 mm and split in distal about 10.0 mm into five branches; about 63.0 mm long and branch diameter about 1.0 mm; color nearest RHS 155D; Stigma: typically five; flattened globose, puberulent, about 3.3 mm in diameter and about 1.5 mm tall; color nearest RHS 160B; Ovary: superior, about 6.5 mm across at base and about 5.5 mm tall; acute apex; color between RHS 145B and RHS 145C.

*Androecium*.—Filaments: numerous, about 150; about 8.0 mm long and about 0.3 mm diameter; attached along nearly the entire length of column; color nearest RHS 155D with blush of nearest RHS 60C in lower column portion; Anthers: flattened ellipsoid; dorsifixed; about 2.0 mm long and 1.5 mm across and about 0.8 mm thick; color nearest RHS 155B; Pollen: abundant, globose, less than 0.1 mm long; color nearest RHS 158D.

Pedicel: Terete, glandular, hirsutulous to sparsely farinose; length from base of sepal to abscission point up to about 1.4 cm long, from abscission point to stem node about 5.8 cm long; about 3.0 mm diameter; longer on early flowers and decreasing in distal flowers; color nearest RHS 146A above and below nearest RHS 146B;

Peduncle: Terete, glabrous, glaucous; about 42.0 cm long and about 1.2 mm diameter before flowers; with about 38 flowers per peduncle; color nearest RHS 183D with undertone of nearest RHS 146D becoming nearest RHS 183D in regions of intense light;

Fruit: Loculicidal capsule; pubescent along inner septa, glabrous outside; globoid, with acute apex and rounded base; about 20.0 mm long and 20.0 mm diameter; color nearest RHS 165A when mature;

Seed: Minutely floccose, globose; about 3.0 mm in diameter; color nearest RHS N200A;

Resistance: *Hibiscus* 'Cherry Choco Latte' has not displayed any pest and disease resistance beyond that typical of hardy perennial *hibiscus*. The plant grows best with plenty of moisture, but is able to tolerate some drought once established.

Hardiness at least from USDA zone 4 through 9, and other disease resistance is typical of that of other hardy *hibiscus* cultivars.

I claim:

1. A new cultivar of hardy herbaceous perennial *Hibiscus* hybrid plant named 'Cherry Choco Latte' as herein illustrated and described.

* * * * *